(12) United States Patent
Porter et al.

(10) Patent No.: US 8,915,970 B2
(45) Date of Patent: Dec. 23, 2014

(54) TRANSDERMAL PROSTHESIS

(71) Applicant: Biomet Manufacturing Corporation, Warsaw, IN (US)

(72) Inventors: Joshua R. Porter, Winona Lake, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 14 days.

(21) Appl. No.: 13/762,744

(22) Filed: Feb. 8, 2013

(65) Prior Publication Data
US 2014/0228973 A1 Aug. 14, 2014

(51) Int. Cl.
A61F 2/78 (2006.01)
A61F 2/74 (2006.01)
A61F 2/28 (2006.01)

(52) U.S. Cl.
CPC .......................................... *A61F 2/78* (2013.01)
USPC ............... 623/32; 623/27; 623/33; 623/16.11

(58) Field of Classification Search
CPC ................................ A61F 2/2814; A61F 2/78
USPC .................... 623/16.11, 23.44, 27, 32, 33, 54
See application file for complete search history.

(56) References Cited

U.S. PATENT DOCUMENTS

| | | | |
|---|---|---|---|
| 408,080 A | 7/1889 | Carroll | |
| 583,455 A | 6/1897 | Bush | |
| 1,217,637 A | 2/1917 | Rink | |
| 2,397,545 A | 4/1946 | Hardinge | |
| 3,067,740 A | 12/1962 | Haboush | |
| 3,740,769 A | 6/1973 | Haboush | |
| 3,947,897 A | 4/1976 | Owens | |
| 4,011,861 A | 3/1977 | Enger | |
| 4,016,874 A | 4/1977 | Maffei et al. | |
| 4,080,666 A | 3/1978 | Fixel | |
| 4,129,903 A | 12/1978 | Huggler | |
| 4,158,895 A * | 6/1979 | Frosch et al. | 606/60 |
| 4,183,357 A | 1/1980 | Bentley et al. | |
| 4,245,360 A | 1/1981 | Brinckmann et al. | |

(Continued)

FOREIGN PATENT DOCUMENTS

| | | |
|---|---|---|
| DE | 293485 | 6/1929 |
| DE | 3605630 | 9/1987 |

(Continued)

OTHER PUBLICATIONS

Sullivan, Uden, Robinson, Sooriakumaran. Rehabilitation of the trans-femoral amputee with an osseointegrated prosthesis: the United Kingdom experience. 2003, Prosthetics and Orthotics International. 27, 114-120.*

(Continued)

*Primary Examiner* — Thomas J Sweet
*Assistant Examiner* — Christie Bahena
(74) *Attorney, Agent, or Firm* — Harness, Dickey

(57) ABSTRACT

A transdermal implant assembly including a transdermal bone fixator configured for anchoring into a bone. The fixator includes a longitudinally extending shaft configured to be received into a recess of the bone, and a spindle defining a cavity. A compliant biasing member is disposed within the cavity and an end cap is removably coupled to the spindle to seal the cavity. The compliant biasing member is accessible for adjustments from the external environment.

23 Claims, 12 Drawing Sheets

(56) References Cited

U.S. PATENT DOCUMENTS

| | | | |
|---|---|---|---|
| 4,262,665 A | 4/1981 | Roalstad et al. | |
| 4,314,381 A | 2/1982 | Koeneman | |
| 4,321,914 A | 3/1982 | Begovac et al. | |
| 4,502,160 A | 3/1985 | Moore et al. | |
| 4,534,761 A | 8/1985 | Raible | |
| 4,547,912 A * | 10/1985 | Sherva-Parker | 623/16.11 |
| 4,578,063 A | 3/1986 | Inman et al. | |
| 4,586,932 A | 5/1986 | Scales | |
| 4,621,629 A | 11/1986 | Koeneman | |
| 4,623,352 A | 11/1986 | Oh | |
| 4,644,943 A | 2/1987 | Thompson et al. | |
| 4,645,504 A | 2/1987 | Byers | |
| 4,673,407 A | 6/1987 | Martin | |
| 4,682,590 A | 7/1987 | Kothmann | |
| 4,781,720 A | 11/1988 | Sherva-Parker | |
| 4,822,366 A | 4/1989 | Bolesky | |
| 4,827,918 A | 5/1989 | Olerud et al. | |
| 4,883,489 A | 11/1989 | Grundei et al. | |
| 4,892,551 A | 1/1990 | Haber | |
| 4,897,081 A | 1/1990 | Poirier et al. | |
| 4,904,264 A | 2/1990 | Scheunemann et al. | |
| 4,923,472 A | 5/1990 | Ugolini | |
| 4,938,768 A | 7/1990 | Wu | |
| 4,946,459 A | 8/1990 | Bradshaw et al. | |
| 4,947,502 A | 8/1990 | Engelhardt | |
| 4,955,910 A | 9/1990 | Bolesky | |
| 4,959,064 A | 9/1990 | Engelhardt | |
| 4,959,072 A | 9/1990 | Morscher et al. | |
| 4,986,834 A | 1/1991 | Smith et al. | |
| 5,007,935 A | 4/1991 | Vincent et al. | |
| 5,007,936 A | 4/1991 | Woolson | |
| 5,030,220 A | 7/1991 | Howland | |
| 5,035,711 A | 7/1991 | Aoki et al. | |
| 5,035,712 A | 7/1991 | Hoffman et al. | |
| 5,057,101 A | 10/1991 | Dorr et al. | |
| 5,057,103 A | 10/1991 | Davis | |
| 5,071,435 A | 12/1991 | Fuchs et al. | |
| 5,108,398 A | 4/1992 | McQueen et al. | |
| 5,112,333 A | 5/1992 | Fixel | |
| 5,133,760 A | 7/1992 | Petersen et al. | |
| 5,156,625 A | 10/1992 | Marchetti et al. | |
| 5,180,383 A | 1/1993 | Haydon | |
| 5,181,928 A | 1/1993 | Bolesky et al. | |
| 5,197,989 A | 3/1993 | Hinckfuss et al. | |
| 5,201,881 A | 4/1993 | Evans | |
| 5,267,999 A | 12/1993 | Olerud et al. | |
| 5,281,226 A | 1/1994 | Davydov et al. | |
| 5,326,360 A | 7/1994 | Kotz et al. | |
| 5,326,367 A | 7/1994 | Robioneck et al. | |
| 5,326,368 A | 7/1994 | Collazo | |
| 5,332,398 A | 7/1994 | Miller et al. | |
| 5,334,184 A | 8/1994 | Bimman | |
| 5,352,227 A | 10/1994 | O'Hara | |
| 5,356,410 A | 10/1994 | Pennig et al. | |
| 5,358,524 A | 10/1994 | Richelsoph | |
| 5,389,107 A | 2/1995 | Nassar et al. | |
| 5,405,388 A | 4/1995 | Fox | |
| 5,411,504 A | 5/1995 | Vilas | |
| 5,478,237 A | 12/1995 | Ishizawa | |
| 5,489,306 A | 2/1996 | Gorski | |
| 5,507,747 A | 4/1996 | Yuan et al. | |
| 5,507,827 A | 4/1996 | Grundei et al. | |
| 5,549,692 A | 8/1996 | Hauser et al. | |
| 5,658,288 A | 8/1997 | Kim | |
| 5,743,908 A | 4/1998 | Kim | |
| 5,800,553 A | 9/1998 | Albrektsson et al. | |
| 5,800,557 A | 9/1998 | Elhami et al. | |
| 5,824,078 A | 10/1998 | Nelson et al. | |
| 5,827,285 A | 10/1998 | Bramlet | |
| 5,871,540 A | 2/1999 | Weissman et al. | |
| 5,871,548 A | 2/1999 | Sanders et al. | |
| 5,882,351 A | 3/1999 | Fox | |
| 5,916,268 A | 6/1999 | Schollner et al. | |
| 5,928,232 A | 7/1999 | Howland et al. | |
| 5,941,881 A | 8/1999 | Barnes | |
| 5,951,555 A | 9/1999 | Rehak et al. | |
| 5,981,828 A | 11/1999 | Nelson et al. | |
| 5,990,382 A | 11/1999 | Fox | |
| 6,051,007 A | 4/2000 | Hogendijk et al. | |
| 6,162,257 A | 12/2000 | Gustilo et al. | |
| 6,197,065 B1 * | 3/2001 | Martin et al. | 623/23.17 |
| 6,200,317 B1 | 3/2001 | Aalsma et al. | |
| 6,273,891 B1 | 8/2001 | Masini | |
| 6,293,971 B1 | 9/2001 | Nelson et al. | |
| 6,302,918 B1 | 10/2001 | Gramnas | |
| 6,336,929 B1 | 1/2002 | Justin | |
| 6,336,941 B1 | 1/2002 | Subba Rao et al. | |
| 6,387,097 B1 | 5/2002 | Alby et al. | |
| 6,425,925 B1 * | 7/2002 | Grundei | 623/32 |
| 6,458,161 B1 | 10/2002 | Gibbs et al. | |
| 6,482,238 B1 | 11/2002 | Grundei | |
| 6,485,522 B1 | 11/2002 | Grundei | |
| 6,508,841 B2 | 1/2003 | Martin et al. | |
| 6,579,294 B2 | 6/2003 | Robioneck | |
| 6,656,184 B1 | 12/2003 | White et al. | |
| 6,712,778 B1 * | 3/2004 | Jeffcoat et al. | 600/590 |
| 6,712,855 B2 | 3/2004 | Martin et al. | |
| 6,740,089 B2 | 5/2004 | Haider | |
| 6,786,910 B2 | 9/2004 | Cohen et al. | |
| 6,840,919 B1 | 1/2005 | Håkansson | |
| 6,840,959 B2 | 1/2005 | Treacy et al. | |
| 6,843,808 B2 | 1/2005 | Grundei | |
| 6,869,450 B2 | 3/2005 | Grundei | |
| 7,014,661 B2 | 3/2006 | Blunn et al. | |
| 7,018,420 B2 | 3/2006 | Grundei | |
| 7,101,403 B2 | 9/2006 | Chen | |
| 7,141,073 B2 | 11/2006 | May et al. | |
| 7,150,762 B2 | 12/2006 | Caspers | |
| 7,172,574 B2 | 2/2007 | Lundgren et al. | |
| 7,323,013 B2 | 1/2008 | McTighe et al. | |
| 7,374,577 B2 | 5/2008 | Kim et al. | |
| 7,476,254 B2 | 1/2009 | White et al. | |
| 7,578,851 B2 | 8/2009 | Dong et al. | |
| 7,604,617 B2 | 10/2009 | Porter et al. | |
| 7,674,426 B2 | 3/2010 | Grohowski, Jr. | |
| 7,704,225 B2 | 4/2010 | Kantrowitz | |
| 7,722,678 B2 * | 5/2010 | Brown et al. | 623/32 |
| 7,766,881 B2 | 8/2010 | Reinmann | |
| 7,909,883 B2 | 3/2011 | Sidebotham | |
| 8,075,630 B2 | 12/2011 | Ricci et al. | |
| 2001/0051831 A1 | 12/2001 | Subba Rao et al. | |
| 2002/0099449 A1 | 7/2002 | Speitling | |
| 2003/0028249 A1 | 2/2003 | Baccelli et al. | |
| 2003/0109878 A1 | 6/2003 | Grundei | |
| 2003/0130659 A1 | 7/2003 | Haider | |
| 2003/0171825 A1 | 9/2003 | Blunn et al. | |
| 2003/0195636 A1 | 10/2003 | Coop | |
| 2004/0006396 A1 | 1/2004 | Ricci et al. | |
| 2004/0138663 A1 | 7/2004 | Kosashvili et al. | |
| 2004/0148021 A1 | 7/2004 | Cartledge et al. | |
| 2004/0172138 A1 | 9/2004 | May et al. | |
| 2005/0102038 A1 | 5/2005 | Grundei | |
| 2005/0119758 A1 | 6/2005 | Alexander et al. | |
| 2005/0246032 A1 | 11/2005 | Bokros et al. | |
| 2006/0041318 A1 | 2/2006 | Shannon | |
| 2006/0241779 A1 | 10/2006 | Lakin | |
| 2007/0073412 A1 | 3/2007 | Blunn et al. | |
| 2008/0058957 A1 * | 3/2008 | Newcombe et al. | 623/32 |
| 2008/0281421 A1 | 11/2008 | Cahn et al. | |
| 2009/0005820 A1 * | 1/2009 | Bloebaum et al. | 606/302 |
| 2009/0149966 A1 | 6/2009 | Blunn et al. | |
| 2009/0292368 A1 | 11/2009 | Plowman et al. | |
| 2010/0204802 A1 | 8/2010 | Wilson et al. | |
| 2011/0029002 A1 | 2/2011 | Mann et al. | |
| 2011/0190907 A1 * | 8/2011 | Porter et al. | 623/32 |
| 2012/0135133 A1 * | 5/2012 | O'Neill et al. | 427/2.27 |
| 2012/0143512 A1 | 6/2012 | Tompkins | |
| 2012/0150149 A1 | 6/2012 | Kantrowitz | |
| 2012/0232602 A1 * | 9/2012 | Tomaszewski et al. | 606/86 R |

FOREIGN PATENT DOCUMENTS

| | | |
|---|---|---|
| DE | 19931882 | 5/2001 |
| FR | 2519248 | 7/1983 |

(56) References Cited

FOREIGN PATENT DOCUMENTS

| | | |
|---|---|---|
| GB | 2139095 A | 11/1984 |
| JP | 61200903 | 9/1986 |
| JP | 04183463 A | 6/1992 |
| SU | 1181652 A1 | 9/1985 |
| WO | WO-9635387 | 11/1996 |
| WO | WO-9829058 | 7/1998 |
| WO | WO-0027298 | 5/2000 |
| WO | WO-0143652 | 6/2001 |
| WO | WO-02071962 | 9/2002 |

OTHER PUBLICATIONS

Jennings. Doctors grow new ear on cancer victim's arm. Sep. 29, 2012. ABC News.*

"COMPRESS Compliant Pre-Stress", brochure, Biomet Orthopedics, Inc. 2009. 42 sheets.

"Endo-Exo: New! Endo-Exo Prosthesis", Eska Australia, Specialists in Orthopaedic Implants, Product Review, http://www.eskaaustralia.com.au/products_endo.html, accessed Aug. 1, 2011.

"Limb Salvage Product Portfolio", brochure, Biomet Orthopedics, Inc. 2009. 23 sheets.

"Regenerex Porous Titanium Construct", brochure, Biomet Orthopedics, Inc. 2008. 7 sheets.

"The Osseotite® Implant, The Surface That Succeds. Proven Performance and Predictable Outcomes", brochure, Biomet 3I LLC, Inc. 2009. 8 sheets.

"The Osseotite® Implant—Documented Success", brochure, Biomet 3i LLC, Inc. Apr. 2012. 8 sheets.

Aboulafia, Albert J., et al., "Reconstruction Using the Saddle Prosthesis Following Excision of Primary and Metastic Periacetabular Tumors" (1995), Clinical Orthopaedics and Related Research, No. 314, pp. 203-213.

Branemark, Rickard et al., "Osseointegration in skeletal Reconstruction and Rehabilitation", Journal of Rehabilitation Research & Development, vol. 38 No. 2, Mar./Apr. 2001, 8 pages, http://www.rehab.research.va.gov/jour/01/38/2/brane382.htm accessed Jul. 29, 2011.

European Search Report mailed Jul. 21, 2005 for pending European Application No. EP05251364.

Fitzpatrick, Noel, "Intraosseous Transcutaneous Amputation Prosthesis, An Alternative to Limb Amputation in Dogs and Cats", Society of Practising Veterinary Surgeons, SPVS Review 2009, pp. 2-5.

Isackson, Dorthyann . . . Kent N. Bachus, et al., "Dermal Barriers to Prevent Infection of Percutaneous Implants", abstract, Society for Biomaterials, Translational Research Symposium, Sep. 11-13, 2008, Atlanta, Georgia.

Martin, D.L., M.D., et al., "Comparison of Cortical Bone Loss is Segmental Bone Prosthetic Replacement: Cemented Stem vs. Compliant Fixation".

Mueckley, Thomas, et al., "Compression Nailing of Long Bones", European Journal of Trauma (2003) No. 3 pp. 113-128.

Pendergrass, et al., "Sealing the skin barrier around transcutaneous implants", The Journal of Bone and Joint Surgery, vol. 90-B, No. 1, pp. 114-121, Jan. 2008.

Pitkin, Mark et al., "Skin and bone integrated prosthetic pylon: A pilot animal study", Journal of Rehabilitation Reseasrch & Development, vol. 43, No. 4, pp. 573-580, Jul./Aug. 2006.

Satcher, Jr., Robert, et al., "Reconstruction of the Pelvis After Resection of Tumors About the Acetabulum", (2003), Clinical Orthopaedics and Related Research, No. 409, pp. 209-217.

\* cited by examiner

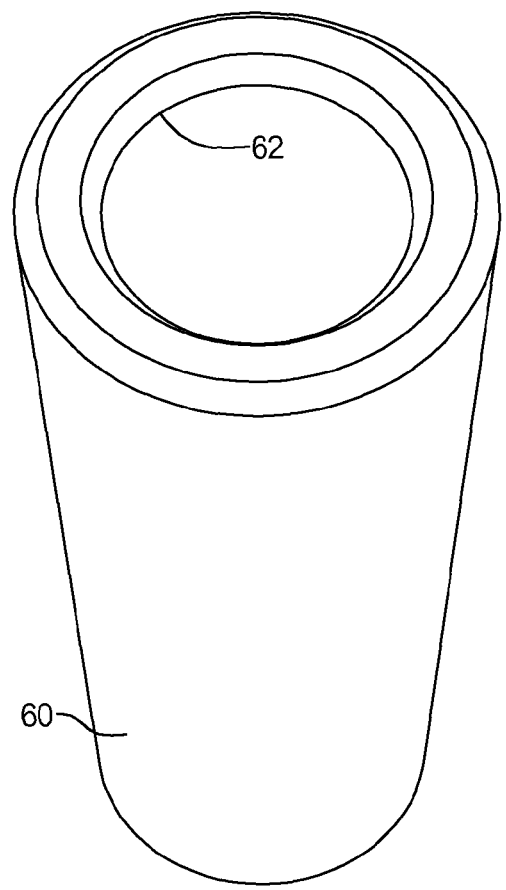
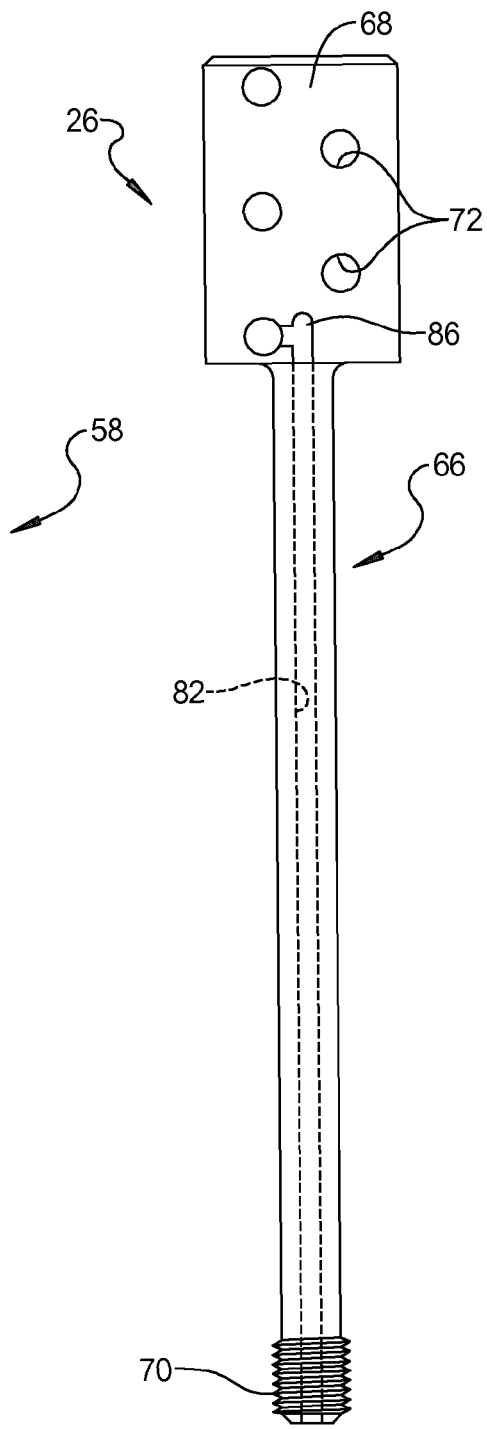
FIG 10
FIG 11

TRANSDERMAL PROSTHESIS

INTRODUCTION

The present technology generally relates to prostheses, and specifically relates to transdermal medical implant devices, and methods of their implantation.

Various external fixation devices to treat amputation or trauma include compliant mechanisms for supporting a prosthetic device to a bone. In devices of this type, a compliant fixation mechanism may provide a compressive stress at the bone interface for preventing bone resorption over time. Typically, a metal portion of the fixation device may extend beyond the cut surface of the bone, such that soft tissue contacts the metal portion, rather than the bone.

In standard compress implants, a predetermined spring force may be chosen when implanted to the bone, with the intent of providing a constant compressive force exerted upon the bone between an anchor plug and a face of the implant near the dermal layer. If the implant subsides over time, however, some of the spring force may be lost because the compliant mechanism is compressed less. Because the standard compress implant is entirely disposed within the body of a patient, it cannot be adjusted without additional surgical procedures.

SUMMARY

The present teachings provide transdermal medical implant devices with access to the interior of the implant via at least one end of the implant that may be disposed outside of the body. The exposed access may minimize or eliminate the need for any surgical procedure to make force adjustments. Also, the external access can allow for the monitoring of various features related to the implant.

The present teachings provide a transdermal implant assembly for attaching an external prosthesis to a bone of a patient. In certain aspects, the assembly includes a transdermal bone fixator configured for anchoring into a recess of the bone. The transdermal bone fixator includes a longitudinally extending shaft configured to be received into the recess of the bone, and a spindle defining a cavity. The spindle has a proximal end and a distal end, wherein the distal end extends a distance past a dermis layer of the patient and is exposed to an environment external from the bone of the patient. A compliant biasing member is disposed within the cavity; and an end cap is removably coupled to the spindle and configured to seal the cavity. A prosthesis adapter is coupled to the spindle and configured for connection to an external prosthetic device. The compliant biasing member is accessible for adjustments from the external environment.

In further aspects, the transdermal implant assembly includes an anchor disposed in and secured to a recess formed in the bone. The anchor includes a longitudinally extending stem. A transdermal bone fixator is coupled to the anchor and includes a longitudinally extending shaft configured to be received into the recess, and a spindle defining a cavity. The spindle has a proximal end and a distal end, wherein the distal end extends a distance past a dermis layer of the patient and is exposed to an environment external from the patient. An ingrowth collar is disposed between the shaft and the proximal end of the spindle and configured for transcutaneous implantation. A compliant biasing member is disposed within the cavity, pre-stressed and configured to provide a compressive force to the bone. An adjustment member is disposed in the cavity and threadably coupled to the stem of the anchor. The adjustment member is accessible from the external environment for adjusting the compliant biasing member. A prosthesis adapter is coupled to the spindle and configured for connection to an external prosthetic device that is configured for use with the bone. At least one sensor is provided, configured to measure an operational parameter of the transdermal implant.

The present teachings also disclose a method of implanting a transdermal implant assembly into a patient. The method includes exposing and preparing a bone to receive a transdermal bone fixator. The transdermal bone fixator comprises a longitudinally extending shaft configured to be received into the bone, and a spindle having a proximal end and a distal end. The distal end is configured to extend a distance past a dermis layer of the patient. A compliant biasing member is disposed within an interior of the spindle. The shaft of the transdermal bone fixator is implanted into the bone. At least a portion of the spindle is exposed to an environment external from the patient. The method includes setting a first force of the compliant biasing member and monitoring the force thereafter.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 10 is a perspective view of a patient-specific centering sleeve for use with the transdermal implant assembly according to the present teachings;

FIG. 11 is an exemplary anchor member of the transdermal implant assembly according to the present teachings;

Figure 1:
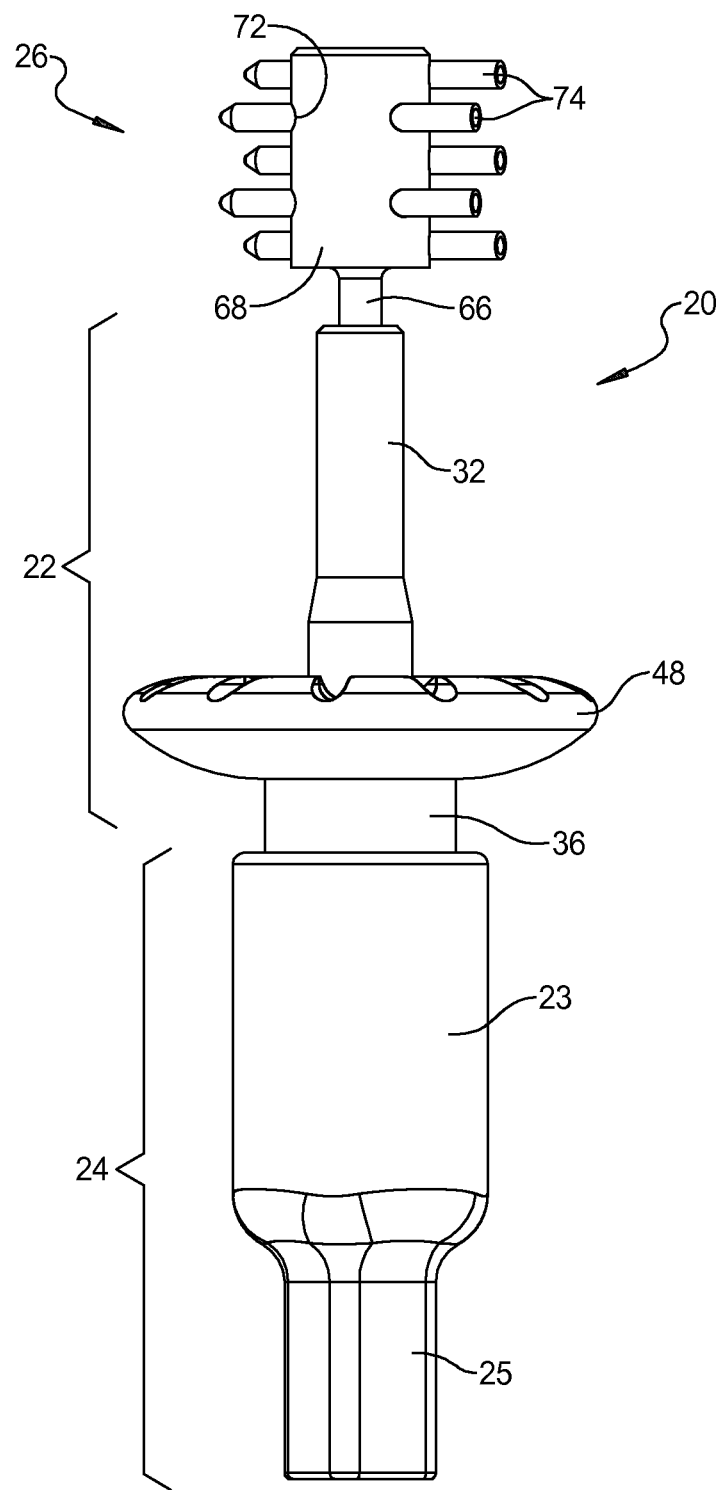
FIG. 1 is a side perspective view of an exemplary transdermal implant assembly device according to the present teachings.
Figure 2:
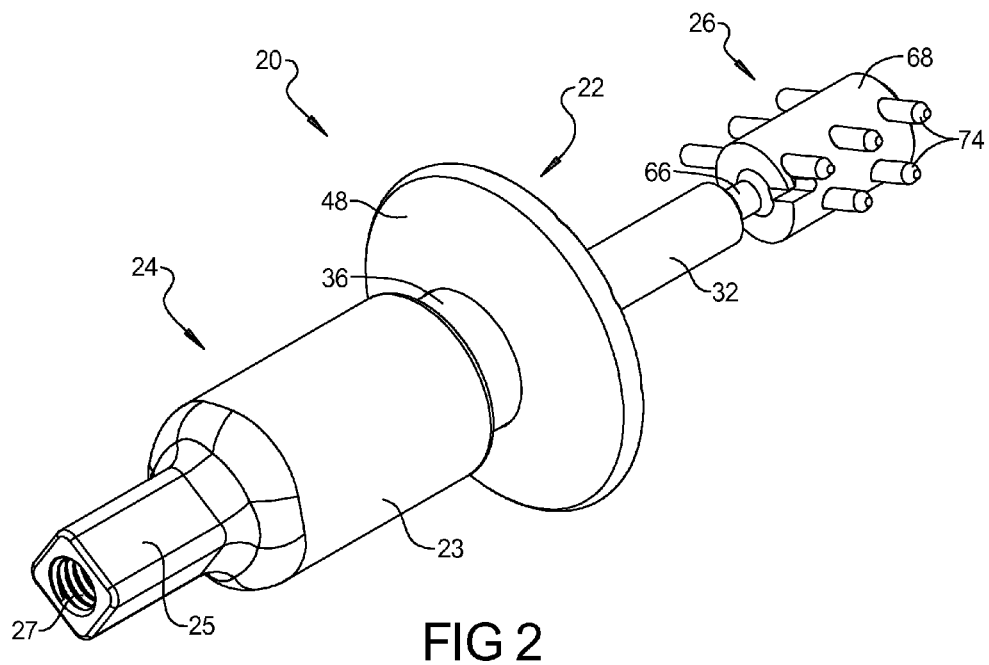
FIG. 2 is a first isometric view of the transdermal implant assembly device of FIG. 1.
Figure 3:
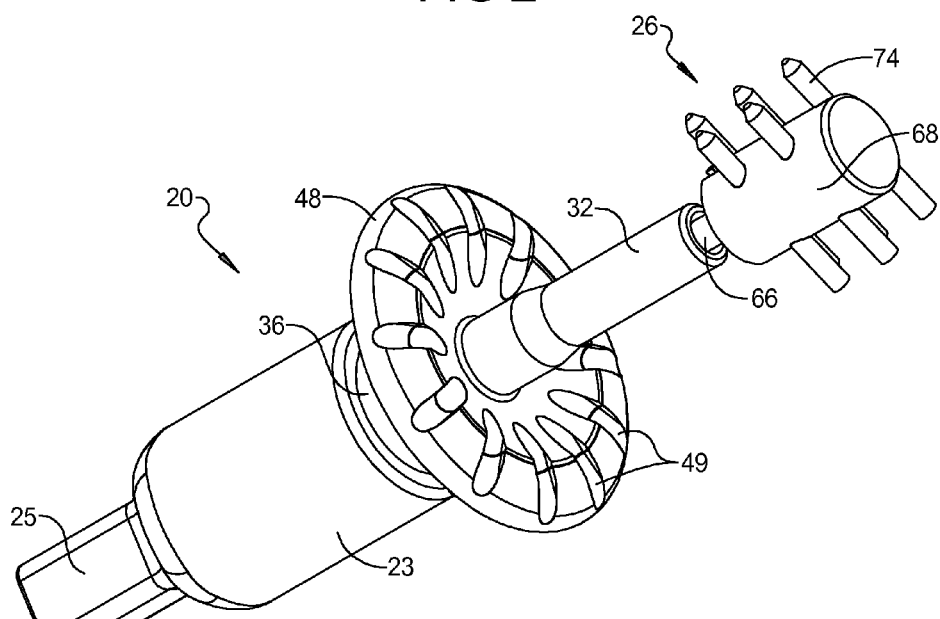
FIG. 3 is a second isometric view of the transdermal implant assembly device of FIG. 1.
Figure 4:
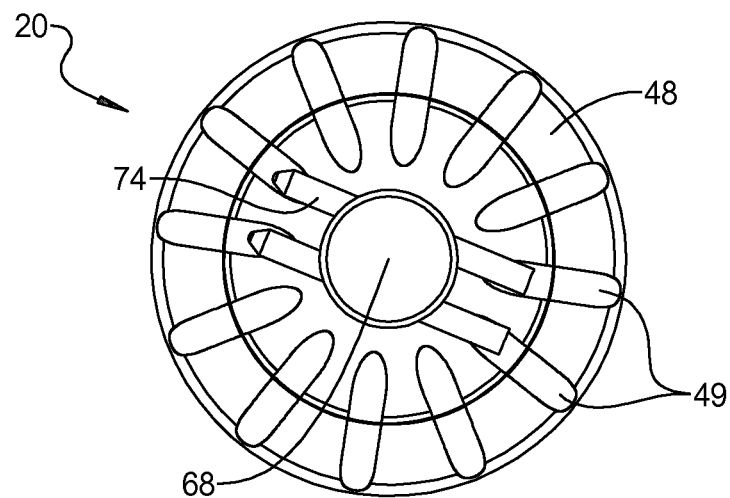
FIG. 4 is a top perspective view of the transdermal implant assembly device of FIG. 1.
Figure 5:
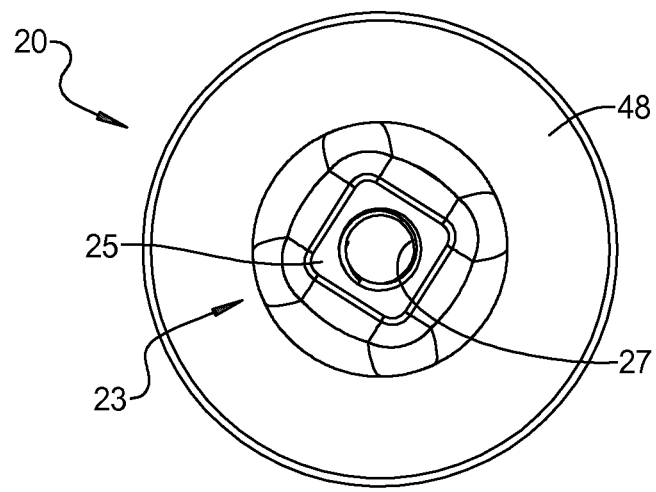
FIG. 5 is a bottom perspective view of the transdermal implant assembly device of FIG. 1.

It should be noted that the figures set forth herein are intended to exemplify the general characteristics of materials, methods, and devices among those of the present technology, for the purpose of the description of certain embodiments. These figures may not precisely reflect the characteristics of any given embodiment, and are not necessarily intended to define or limit specific embodiments within the scope of this technology.

DESCRIPTION OF VARIOUS EMBODIMENTS

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

The present technology generally relates to transdermal medical implant components and methods for improving the strength and usefulness of medical implants. As used herein, the term "implant" may be used to refer to an entire implant, or a portion thereof; portions may be as large or as small as necessary to accommodate the specific need. For example, an implant made in accordance with the present disclosure, generally including an anchor, transdermal bone fixator, and prosthesis adapter as shown in FIGS. 1-6, may constitute the entire implant, or it may be used with one or more pieces or components that together form a final implant or implant assembly. The present disclosure encompasses a wide variety of therapeutic and cosmetic applications, for human and/or other animal patients, and the specific materials and devices used should be biomedically acceptable. As used herein, such a "biomedically acceptable" material or component is one that is suitable for use with humans and/or animals without undue adverse side effects (such as toxicity, irritation, and allergic response) commensurate with a reasonable benefit risk/ratio.

It is envisioned that the present teachings can be used for attaching various types of external prosthetic devices to a bone through a patient's skin via a transdermal implant assembly 20. With reference to FIGS. 1-6, the transdermal implant assembly 20 can generally include a transdermal bone fixator 22, a prosthesis adapter 24, and an anchor member 26. The anchor member 26 may be disposed within and secured to a bore 28 formed within a bone 30, operable to secure the transdermal implant assembly 20 to the bone 30. The transdermal bone fixator 22 may include a longitudinally extending shaft 32 configured to be received into a recess 34 defined by the bore 28, the bore 28 may be an intramedullary canal in the bone 30 (such as a femur, tibia, humerus, etc.) that will receive the external prosthetic device. In various embodiments, the transdermal bone fixator 22 makes use of a compliant biasing member 50, for example, one that can provide pre-stress to form a bone biasing force, to a portion of a bone. It should be understood, however, that in certain aspects a non-compliant fixator in the form of a static (non-dynamic) anchoring member may also be used.

Compliance, as used herein, is a measurement of softness as opposed to stiffness of a material. Compliance of a structural member is generally the reciprocal of Young's modulus (one dimension) or the inverse of the stiffness matrix (more than one dimensions). Accordingly, a compliant member is generally a structural member that has enhanced compliance, such as an elastic spring, bellows, Belleville washers, and other elastically biasing members. The compliant biasing member 50 of the present teachings may allow osseointegration at the bone/implant interface and can provide a stable, high-pressure/implant interface. The compliant biasing member 50 can also assist in the prevention of stress shielding and any concomitant bone loss. Preferably, the compliant biasing member 50 may be adapted to provide a compressive load on the bone, thereby reducing bone loss and promoting bone growth. The compliance can exceed that of native bone 30, such that stress shielding does not occur. Additionally, the native bone 30 can experience physiologic dynamic compressive loading biased by a preset spring compression. In this context, evidence of bone hypertrophy or lack of bone loss may occur near the resection level resulting in increased bone strength, possibly as a result of a phenomenon known as Wolf's Law. It is envisioned that any known compliant fixator can be used, including, but not limited to, the compliant fixators disclosed in U.S. Pat. Nos. 7,141,073; 6,712,855; 6,508,841; and 6,197,065, all of which are assigned to common assignee Biomet Manufacturing Corp., and are incorporated herein by reference. The compliant biasing member 50 can include one or more compliant elements, such as one or more Belleville washers, as shown in FIG. 8, or other spring washers or a single or double helical spring. Detailed descriptions of the structure and operation of various compliant fixators and biasing mechanisms are provided in the above-referenced patents.

Figure 6A:
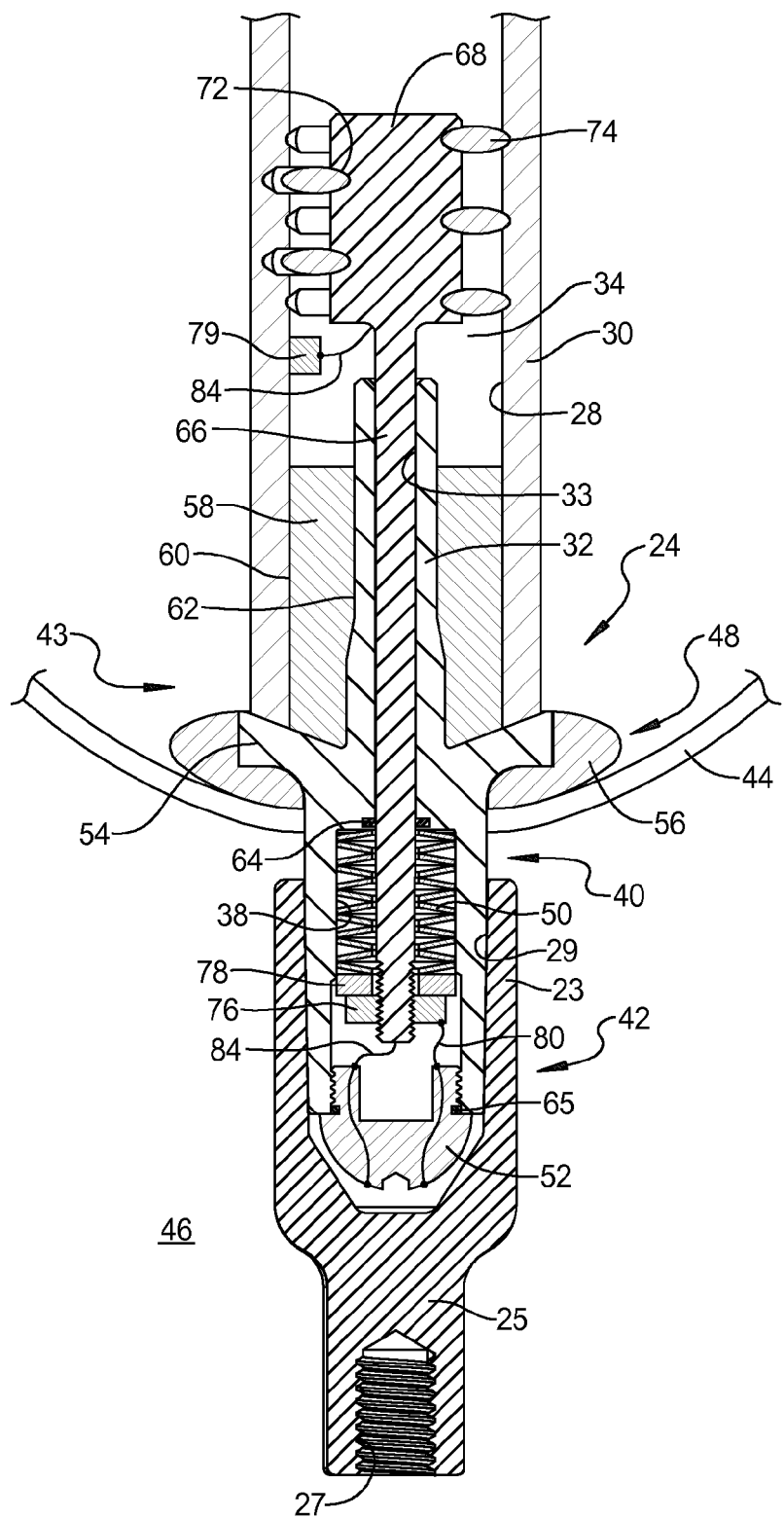
FIG. 6A is a partial cross-sectional view of the transdermal implant assembly device of FIG. 1 shown implanted within a portion of a bone according to one aspect of the present teachings.

With specific reference to FIG. 6A, the transdermal bone fixator 22 may have a spindle 36 disposed opposite the longitudinally extending shaft 32 and generally cylindrical in shape. The spindle 36 may define a longitudinal bore forming an internal cavity 38. The compliant biasing member 50 can be contained within the cavity 38. The cavity 38 can be shaped and configured for accommodating the compliant biasing member 50, such that the cavity 38 may have a larger diameter for Belleville washers than for a helical spring. The exterior of the spindle 36 can be referred to as having a proximal end 40 and a distal end 42. The distal end 42 extends a distance past an epidermis and dermis layer (skin) 44 of the patient and may be exposed to an external environment 46, for example, external from the bone of the patient. In other words, once implanted, at least a portion of the spindle 36 preferably extends outside of the patient's body, accessible without any surgical procedure.

In certain aspects, the proximal end 40 may also be adjacent sub-dermal soft tissue 43 under the epidermis and dermis layers (skin) 44 of the patient. An end cap 52 may be removably coupled to the distal end 42 of the spindle 36 and configured to seal the cavity 38. According to various aspects of the present teachings, the compliant biasing member 50 is thus accessible for adjustments from the external environment 46 by disengaging the prosthesis adapter 24 and removing the end cap 52.

The transdermal bone fixator 22 can be anchored to the bone 30 and pre-stressed via an anchoring member 26. As best shown in FIGS. 1, 6A, and 11, the anchoring member 26 can include an elongated shaft 66 attached to a plug 68 at a first end and having a threaded distal end portion 70. The plug

68, which can be enlarged relative to the shaft 66, can include a plurality of apertures 72 for receiving transverse bone fixation pins 74. The anchoring member 26 can be inserted through a longitudinal bore 33 that passes through the transdermal bone fixator 22 and through the Belleville washers when used as a compliant biasing member 50. Additional specific descriptions of other exemplary anchors in relation to compliant biasing members can also be found in U.S. Pat. No. 7,722,678 and pending application Ser. No. 13/016,766 (published on Aug. 4, 2011 as U.S. Pub. No. 2011/0190907), the entire specifications of which are incorporated herein by reference.

Figure 6B:
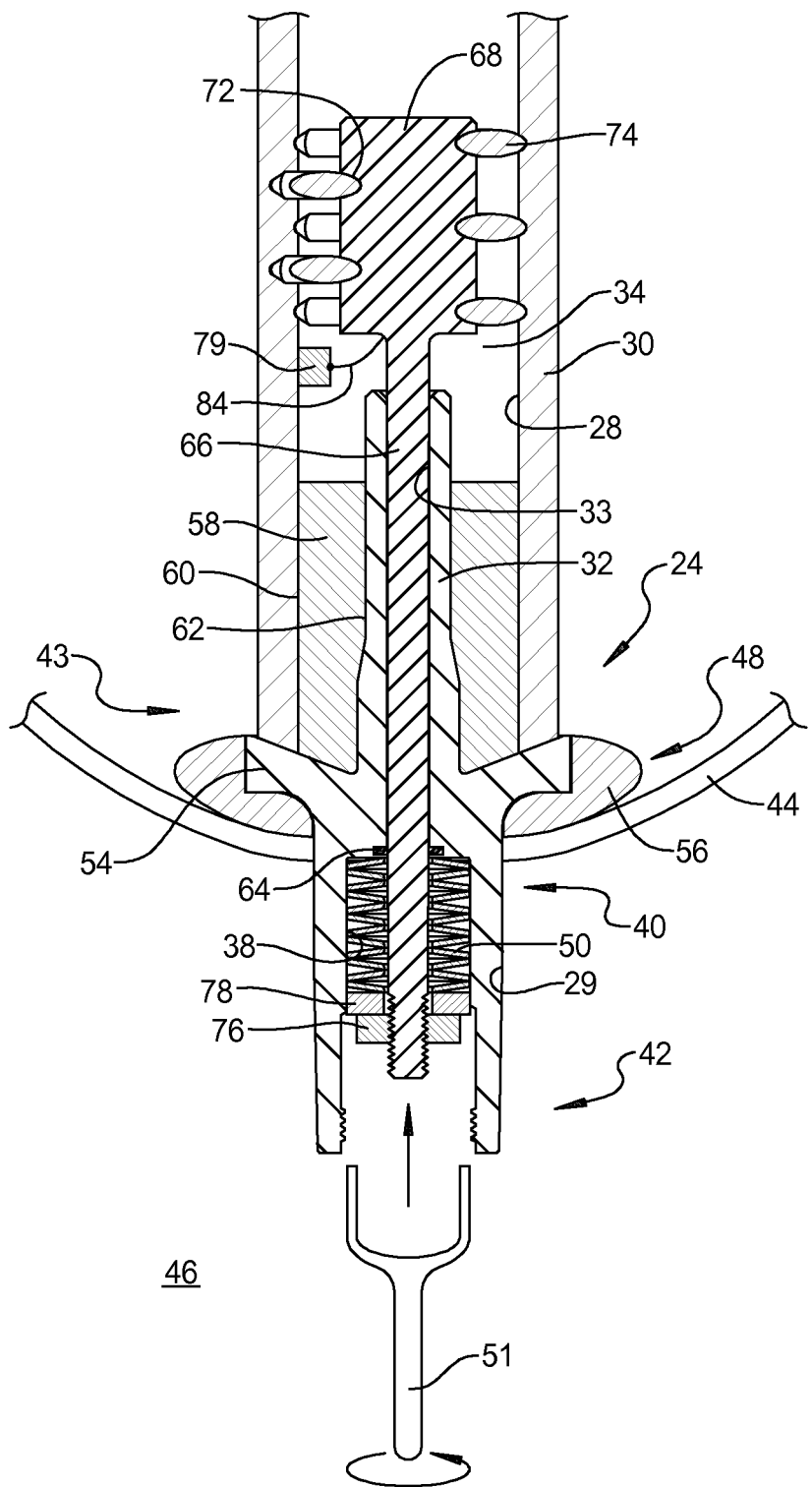
FIG. 6B is a partial cross sectional view of the transdermal implant assembly device illustrating an adjustment of the compliant biasing member.

An adjustment member 76, such as a fastener or nut, can be threadably coupled to the distal threaded portion 70 of the shaft 66 and rotated to a desired location along the shaft 66 in order to pre-stress the compliant biasing member 50 to a exert a preferred amount of force prior to the implantation. After the implantation, the prosthesis adapter 24 and the end cap 52 can be removed as shown in FIG. 6B, exposing the cavity 38 and any internal mechanisms housed therein to the external environment 46 without any need for a surgical procedure or to make an incision in the patient's dermis layer 44. For example, a user can subsequently use a wrench or appropriate adjustment tool 51 to move or adjust the location of the adjustment member 76 along the threaded portion 70 of the anchor shaft 66 in order to compress or expand the compliant biasing member 50, which, in turn, changes the amount of force exerted by the compliant biasing member 50 to the bone.

It should be understood that the specific method of adjusting the force may depend upon the specific type of compliant biasing member 50 that is used. For example, in certain aspects, the compliant biasing member 50 can be adjusted directly, while in other aspects an adjustment member 76 or tubular knob (FIG. 9) is adjusted. Once adjusted, the end cap 52 and prosthesis adapter 24 can then be reattached to the spindle 36, and the force exerted by the compliant biasing member 50 can be monitored, as discussed below. Additional adjustments can be made and repeated as desired. The force may be changed from the first or initial setting to a second setting (different from the first setting), or the force may be adjusted from a second setting (which may have shifted from the first setting) back to the first setting. It is understood that the adjustment can be made numerous times and for various purposes, such as to increase or decrease the force applied by the compliant biasing member 50 to the bone 30. It is also understood that the adjustment tool 51 may be configured to be manipulated external to the transdermal bone fixator 22 and engage and move the adjustment member 76 only by removing at least one member, such as the end cap 52, connected to the transdermal bone fixator 22.

In order to keep the cavity 38 free from foreign objects and to maintain a sterile environment, one or more sealing members 64, 65, such as an elastomeric or silicone O-ring, can be strategically placed at end locations of the cavity 38. In one example, an O-ring 64 can be placed at the interface between the anchor shaft 66 and the cavity 38; in another example, an O-ring 65 can be placed at the interface between the end cap 52 and the cavity 38.

As shown, an ingrowth collar 48 may be disposed between the longitudinally extending shaft 32 and the proximal end 40 of the spindle 36. The ingrowth collar 48 is preferably configured for transcutaneous implantation and may extend laterally relative to the shaft 32. In various aspects, the ingrowth collar 48 can be made of any suitable metal or bioceramic material, including e.g., titanium, cobalt, tantalum, alloys and mixtures thereof, and porous titanium material, such as Regenerex® Porous Titanium Construct, commercially available from Biomet, Inc., Warsaw, Ind. Similarly to the Regenerex® porous titanium construct, a selected porous titanium material may have an average porosity of about 67 percent and pore size (such as a diameter) ranging from about 100 to about 600 microns (including an average of about 300 microns), as well as high strength and flexibility. The ingrowth collar 48 can also be manufactured using additive machining processes known in the art.

In certain aspects, the ingrowth collar 48 may include one or more components or materials. For example, the ingrowth collar 48 may have an outwardly extending base portion 54 with a substantially curved shape and having a biocompatible coating 56 applied thereon. The ingrowth collar 48 can provide a substantially dome-shaped or curved profile disposed adjacent the skin or dermis layers 44. In one aspect, the biocompatible coating 56 can include a porous titanium plasma spray with a hydroxyapatite coating or other similar treatment for increased biologic fixation. The ingrowth collar 48 may be provided with ingrowth bores 49 or other geometrical shapes as may be desired to assist with the integration. In certain embodiments, the transdermal bone fixator 22 may be formed as a monolithic component, including the shaft 32, spindle 36, and ingrowth collar 48 as one piece. In other embodiments, the shaft 32, spindle 36, and ingrowth collar 48 can be modular components that may be removably attached or coupled, or permanently joined together by welding, brazing, soldering, or other known techniques, including mechanical fastening techniques or mechanisms.

As shown, the prosthesis adapter 24 may include a generally cylindrical shaped outer portion 23 that tapers and transforms to a smaller, narrower and substantially square cross-section portion 25 for connection to an external prosthetic device (not shown) that is operable for use with the bone 30. The end of the prosthesis adapter 24 may be provided with connecting threads 27 or other connecting portions or mechanisms, as desired. In various aspects, the generally cylindrical shaped portion 23 of the prosthesis adapter 24 may define a tapered internal bore 29, and the distal end 42 of the exterior of the spindle 36 can be provided with a similarly tapered geometry such that the spindle 36 can be received into and coupled with an interior of the prosthesis adapter 24 via a pressed taper-to-taper connection. Thus, the prosthesis adapter 24 can be impacted in position for locking the tapered connection with the spindle 36. A skin flap around the incision area can be sutured around the proximal end 40 of the spindle.

Referring to FIGS. 6A and 10, the transdermal implant assembly 20 can include a centering sleeve 58 for receiving the shaft 32 of the transdermal bone fixator 22. The centering sleeve 58 can include an outer surface 60 engageable with the bone bore 28 and an inner surface 62 receiving and engaging the shaft 32 of the transdermal bone fixator 22. In some embodiments, the centering sleeve 58 can be patient-specific (customized for an individual patient). For example, the outer surface 60 of the centering sleeve 58 can be patient-specific to conform to the surface of the bone bore 28 based on a three-dimensional image of the bone bore 28. Three-dimensional images of the bone bore 28 can be generated via known techniques, including magnetic resonance imaging (MRI), computerized tomography (CT) or other imaging methods of the patient's anatomy during a pre-operative planning phase of the surgical procedure using computer modeling technology commercially available, for example, by Materialise USA, Plymouth, Mich. The outer surface 60 of the centering sleeve 58 can include a surface structure that is, for example, patient-specific, cylindrical or piece-wise cylindrical, conical, or other curved and closed surface shapes. A patient specific centering sleeve 58 can substantially mirror and/or be complementary to the internal surface of the bore 28. The inner surface 62 of the centering sleeve 58 can be configured to receive and engage a portion of the shaft 32 of standard (non-custom) bone fixators 22 of different standard sizes and can be, for example, tapered, cylindrical, piece-wise cylindrical or piece-wise tapered. In this regard, the centering sleeve 58 provides a transition from a patient-specific engagement with the bone 30 of the patient to a standard engagement with one of the standard size bone fixators 22.

Figure 7:
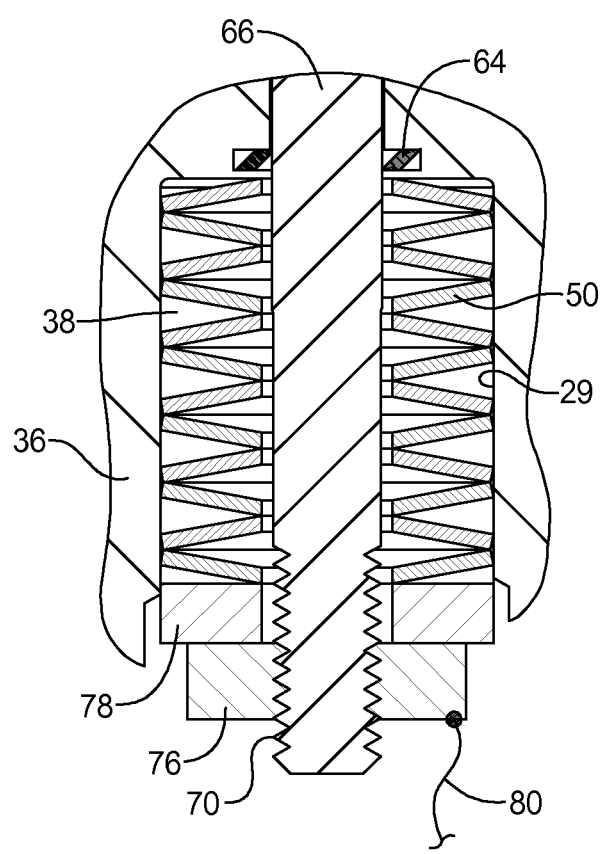
FIG. 7 is a magnified cross-sectional view of a spindle cavity including an exemplary compliant biasing member assembly according to one aspect the present teachings.

In addition to being able to modify the force adjustments related to the compliant biasing member 50, the present teachings also relate to force monitoring and preventative maintenance of the transdermal implant assembly 20. Accordingly, in various aspects, the transdermal implant may include one or more sensors to measure operational parameters. In certain aspects, at least one sensor may be configured to transmit data using wireless communication technology as is known in the art. As best shown in FIGS. 6A and 7, a force detection element or force sensor 78 may be provided as a through-hole bolt load cell, configured to measure a force parameter of the compliant biasing member 50. Other exemplary force sensors include load washers, load buttons, bolt sensors with mounting sensors, strain gauges, etc. As illustrated, electrical leads 80 may be run through the implant, for example, from the force sensor 78 to the end cap 52 such that one could communicate with the sensor 78 from outside the body and detect a residual compressive force. While detecting the forces or other operational parameters, decisions could be made to increase or decrease the force of the compliant biasing member 50 before any potential implant loosening can occur. In addition, this may make it easier on certain patients because of the ability of starting the implant with a low spring force and, after the bone quality improves, the spring force can be increased gradually until the bone quality reaches a level where prosthetic mounting and loading is acceptable.

Anchor plug 68 subsidence within the bone 30 may also be detectable radiographically. Thus, X-rays could be used in combination with strain gauges or force sensors to confirm a decrease, such as a gradual decrease, in compression, which could then be corrected, in one example, by tightening/adjusting the adjustment member 76. Additionally, having physical access to the an end of the transdermal implant assembly 20 may enable the use of ultrasound input and vibration monitoring in an effort to determine how much ingrowth has occurred between the transdermal implant assembly 20 and the bone 30, or to qualify the bone strength.

Similar to force detection, the transdermal implant assembly 20 could be instrumented with one or more additional sensors 79, for example responsive to certain infections, configured to detect changes in at least one physiological parameter including, but not limited to, temperature, pressure, pH, electrical potential, and oxygen saturation. In various aspects, the sensor 79 may be configured to detect biomarkers or microbial and macrophage byproducts in order to monitor for any septic-like environmental conditions.

With reference to FIGS. 6A and 11, the shaft 66 of the anchor member 26 may define a longitudinal channel or recess 82 extending from the threaded portion 70 all the way to an aperture 86 defined in the anchor plug 68. In one example, the recess 82 can be used to pass electrical leads 84 from the sensors 79 that may be disposed within the intramedullary canal or surrounding regions adjacent the bone 30 to the end cap 52 or other portion of the implant that may be accessible from an exterior thereof. In another example, the recess 82 can be used as a fluid or communication passageway, for instance, it could be configured for used in delivering antibiotics from the cavity 38 region directly to the intramedullary canal or surrounding regions or recess 34 of the bone 30.

Aggressive apical epithelial migration, or epithelial downgrowth may be initiated as a normal wound healing process to foreign bodies, such as the transdermal implant assembly 20. If not prevented, this process may result in deep pocket formation and subsequent marsupialization (e.g., exposure through the dermis) of the transdermal implant assembly 20. In contrast, subepithelial connective tissue adhesion to a transdermal implant assembly 20 may prevent epithelial downgrowth and associated complications, such as infection.

Figure 8A:
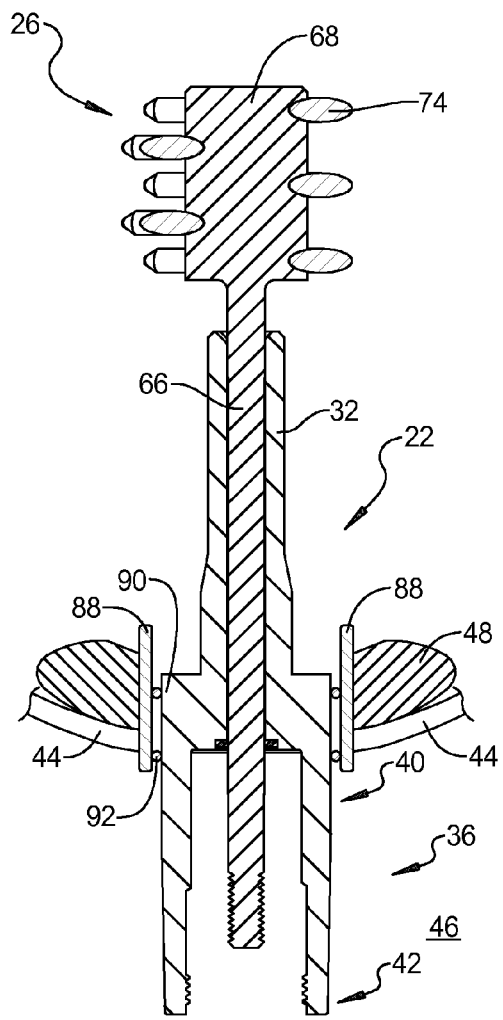
FIGS. 8A-8B are cross-sectional views of a bone fixator and anchor portion of the transdermal implant assembly device of FIG. 1 according to other aspects of the present teachings.
Figure 8B:
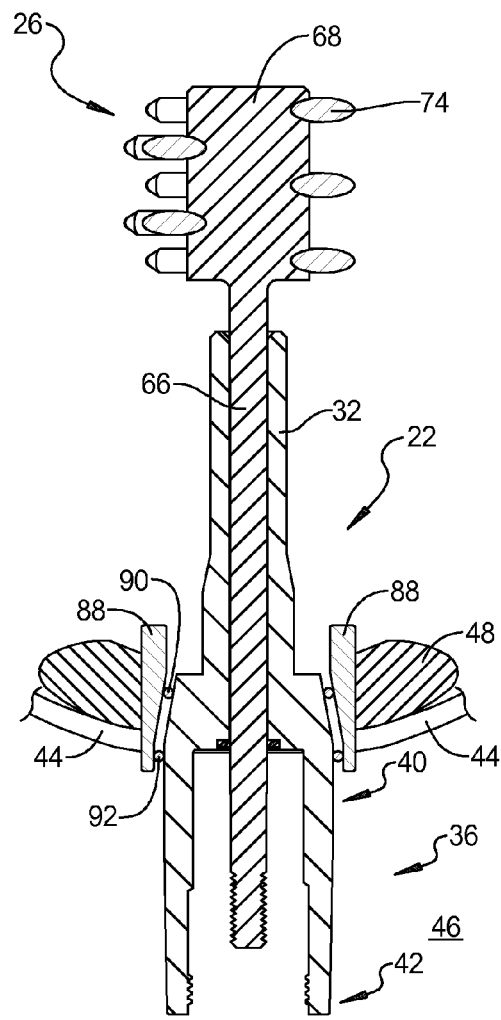

Regarding infection control, and referring to FIGS. 8A-8B, the transdermal implant assembly 20 of the present teachings can include a dermal ingrowth surface or a dermal transition structure 88, such as a substantially cylindrical shaped flange (FIG. 8A) or flange with a tapered interior (FIG. 8B) disposed between the spindle 36 and the ingrowth collar 48, configured to mate with the tapered exterior shape (FIG. 8B) of the spindle 36 and to form a biological seal with the dermis layer 44. The dermal transition structure 88 can alternatively include a porous metal structure surrounding or overlaying a portion of the ingrowth collar 48 of the transdermal bone fixator 22. In certain aspects, the dermal transition structure 88 can also provide a selected roughness gradient to better form a biological seal with the dermis layer 44. Inner and outer elastomeric sealing members 90, 92 may be provided at suitable locations between the spindle 36 and dermal transition structure 88 to maintain an appropriate seal between the body and the external environment 46 and to prevent migration and colonization of bacteria. It may also be important to reduce any shear stress at the skin/implant interface by reducing the mechanical discontinuity (modulus mismatch at the interface). In certain instances, an alginate-impregnated porous construct could be used with the implant of the present teachings. A gel matrix with a tunable modulus could also be molded around a harder porous metal and alleviate any modulus mismatch at the interface during the dermal integration phase. Gel polymerization or cross-linking could be controlled to direct the degradation rate.

Figure 9:
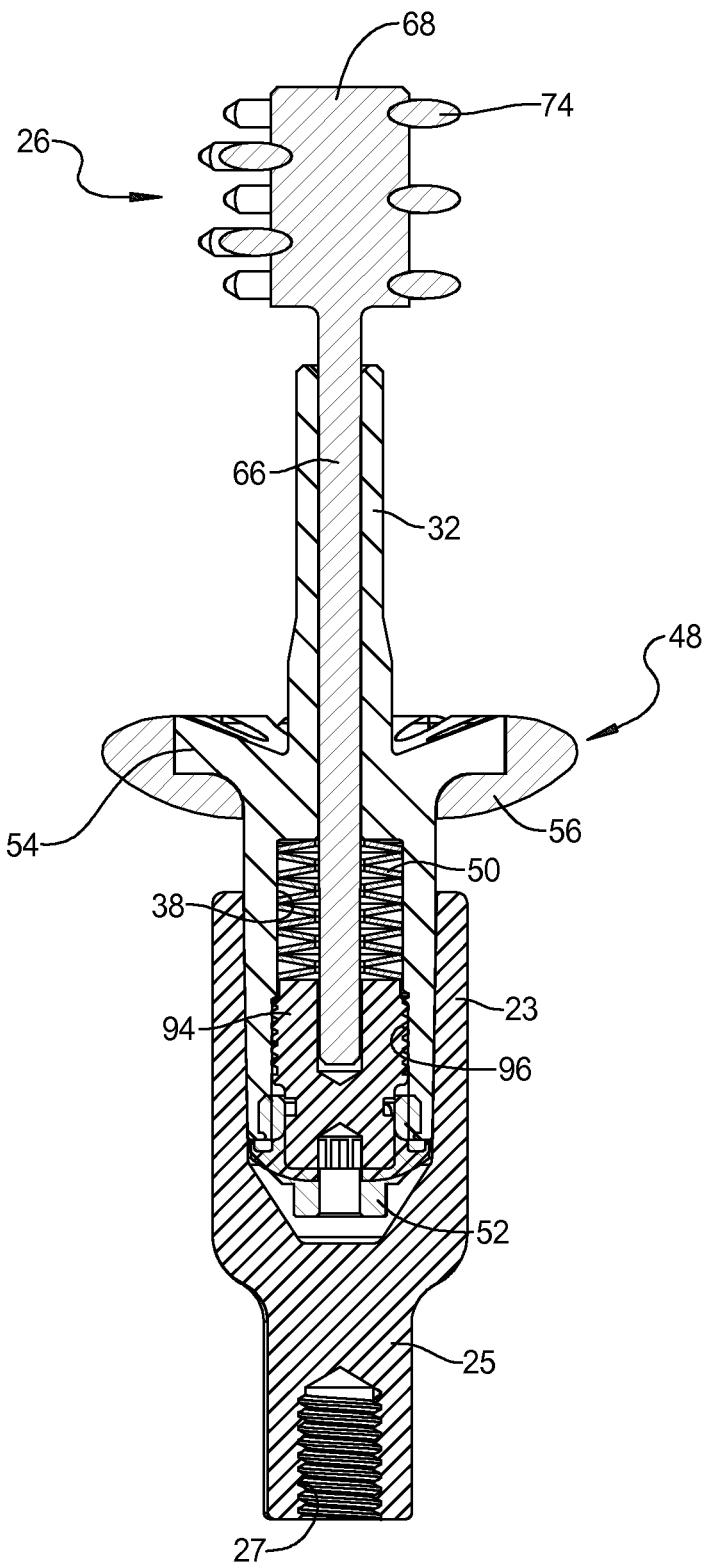
FIG. 9 is a cross-sectional view of the transdermal implant assembly device of FIG. 1 shown according to yet another aspect of the present teachings.

FIG. 9 is a cross-sectional view of the transdermal implant assembly device of FIG. 1 shown according to yet another aspect of the present teachings. In this aspect, the compliant biasing member 50 can be held or secured in place using a tubular knob 94 that may be threadably coupled to a threaded interior bore 96 of the spindle as opposed to being coupled to the shaft 66 of the anchor member 26.

Figure 12:
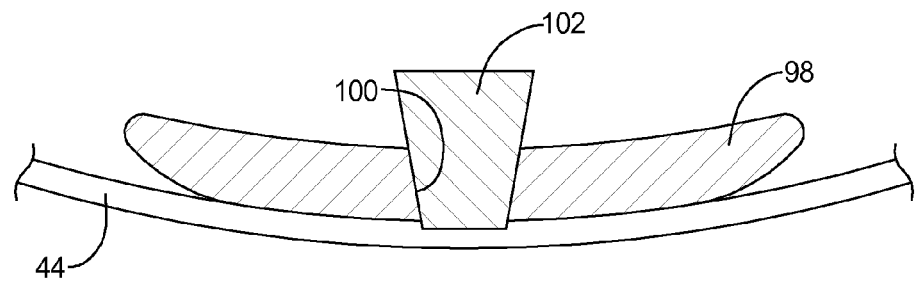
FIG. 12 is a partial cross-sectional view of a porous ingrowth collar and plug member implanted according to one aspect of the present teachings.

The present teachings also provide methods of implanting a transdermal implant assembly into a patient. The methods may be accomplished in separate phases or stages, or the methods could be accomplished by combining the stages during one procedure. In certain aspects, and with reference to FIG. 12, the method may begin with a first stage that includes implanting, below the dermis layer 44 of an implantation site, a porous ingrowth member or collar 98. The implantation site may then be sutured or otherwise closed, allowing the intact dermis layer 44 of the implantation site to integrate with the porous ingrowth collar 98. As shown, the porous ingrowth collar 98 may define a tapered bore 100 and include a removable and tapered plug 102 operable as a temporary placeholder that can be removed prior to the subsequent second stage of the procedure.

After it has been determined that suitable ingrowth and integration at the dermis has occurred, which may take several days or weeks depending upon a variety of factors, the method may continue with a second stage, where a flap or an area of the dermis layer 44 adjacent to and including the porous ingrowth collar 98 is opened and/or resected. The second stage of the procedure may include exposing the bone and allowing for the preparation of the bone for receiving a transdermal implant, stem, etc., or for the implanting of a transdermal port. It should be understood that in addition to being used in conjunction with bone, as described in detail below, the present teachings may also relate to the insertion of fluid channel implants that could be inserted into various subcutaneous environments, for example, intramuscular, subdermal, etc. In the case of a transdermal implant with a transdermal bone fixator 22 as described above, the compliant biasing member 50 can be set to a first force level at this stage of the procedure. The force can subsequently be monitored and adjusted to a second force, as necessary, and the force can continue to be monitored and adjusted throughout the life of the implant by removing the end cap 52 and making appropriate adjustments to the compliant biasing member 50, as discussed above.

Figure 13:
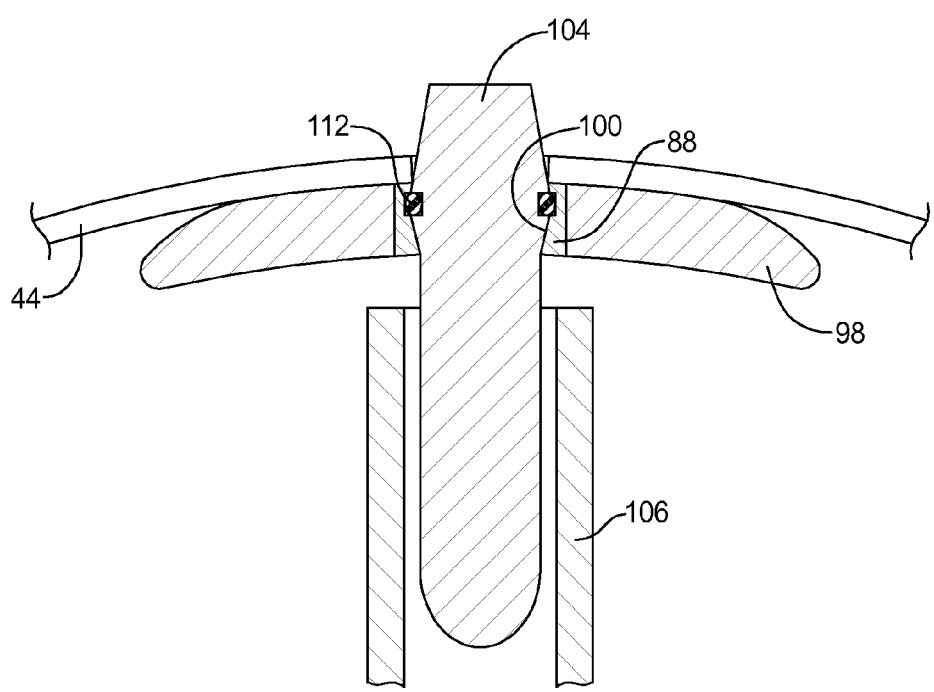
FIG. 13 is a partial cross-sectional view of a porous ingrowth collar and stem implant according to one aspect of the present teachings.

With reference to FIG. 13, a transdermal implant or stem 104 may then be implanted into a bone cortex 106 in the second stage. At least a portion of the stem 104 is configured to pass through the tapered bore 100 defined in the porous ingrowth collar 98. The porous ingrowth collar 98 and skin may be biopsy punched to allow passage of the stem 104 (or spindle) of a transdermal implant.

Figure 14:
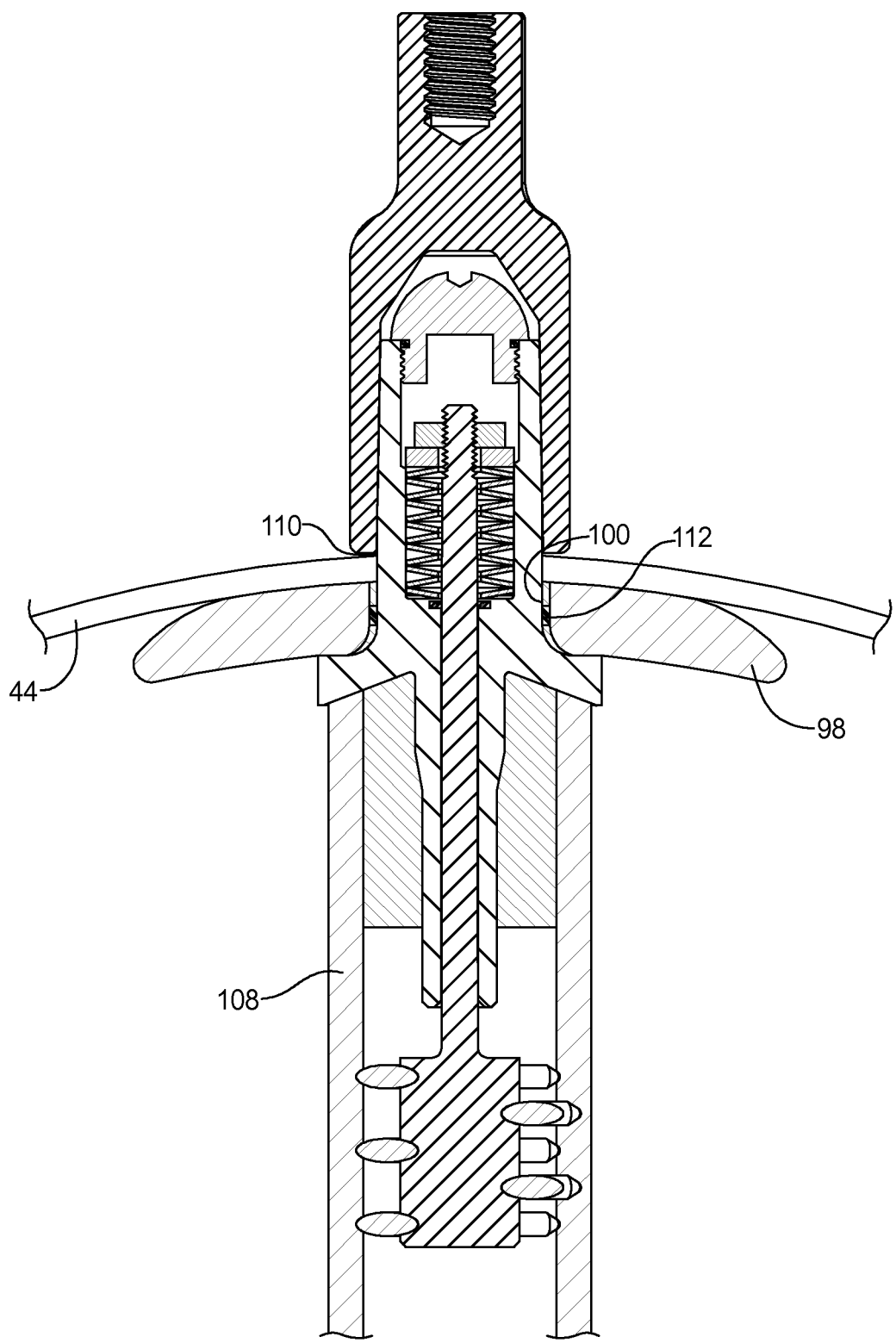
FIG. 14 is a partial cross-sectional view of a porous ingrowth collar and transdermal implant according to one aspect of the present teachings.

With reference to FIG. 14, the second stage of the procedure may alternatively include the implanting of a transdermal implant assembly 20 according to the present teachings, which may be inserted into a cortical bone 108. As shown in FIG. 14, the bore 100 of the porous ingrowth collar 98 and an exterior 110 of the spindle 36 define mating tapered surfaces operable to provide at least a slightly tapered or locking taper junction. A series of silicone gaskets or O-rings 112 may be provided as bacterial barriers. Additionally, thin baffle portions of solid material walls within the porous constructs may be used to prevent bacterial colonization throughout the porous construct in the event part of the porous construct is exposed to the external environment or becomes infected.

Figure 15:
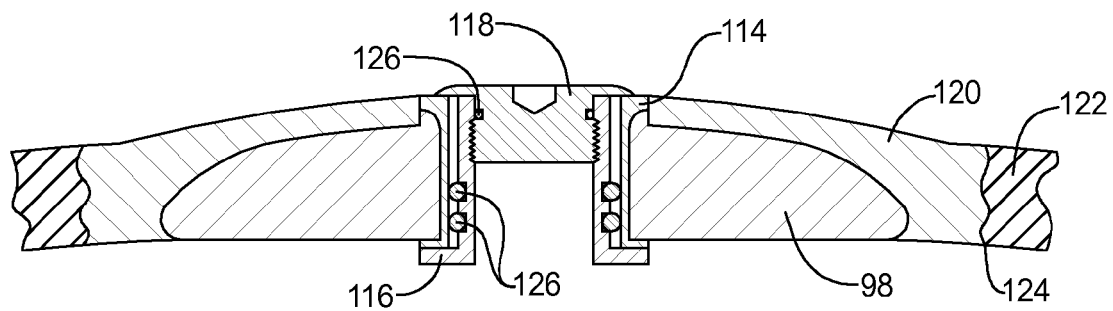
FIG. 15 is a partial cross-sectional view of a transcutaneous port implant according to one aspect of the present teachings.
Figure 16:
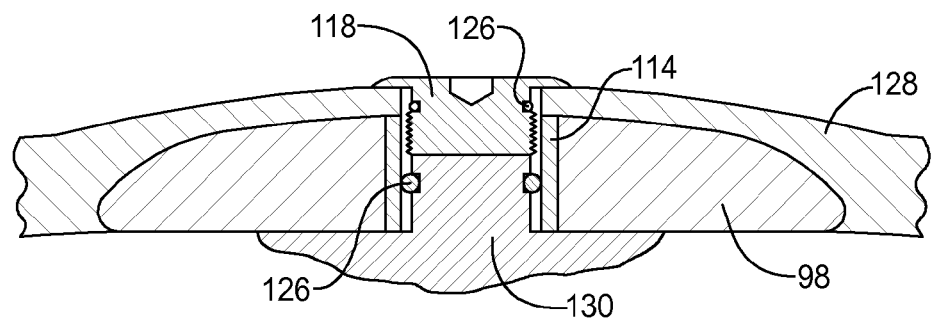
FIG. 16 is a partial cross-sectional view of a transcutaneous port according to another aspect of the present teachings.

In other aspects of the methods, it is contemplated that the porous ingrowth collar 98 may be implanted to integrate with the patient's dermis subcutaneously at a temporary implantation site, and is thereafter resected and grafted (e.g. via sutures) to a final implantation site for use with any of the implants/devices disclosed herein. This method may improve the seal and function as a bacterial barrier between the implant or device and the host soft tissue. As shown in FIG. 15, the implant includes a porous ingrowth collar 98 defining a bore 100 and supporting a transcutaneous port 114 assembly including a cylindrical flange 116 and a sealing cap 118 threadably coupled to an interior of the cylindrical flange 116. Sealing members 126 can be provided as O-rings or gaskets as desired. The implant assembly to be transported away from a first location to a second location may consist of the porous ingrowth collar 98 and port 114 assembly as well as the adjacent donor site tissue 120 from the temporary implantation site. The implant and adjacent tissue would be grafted to the final implant site tissue 122 using attachment features, such as appropriate sutures 124. As shown in FIG. 16, the porous ingrowth collar 98 is implanted subcutaneously in an area different from the final site, then subsequently transplanted to the final implantation site and joined with the a transcutaneous port 114 and sealing cap 116. The existing dermis layer 128 at the final implantation site is laid over the top of the porous ingrowth collar 98 which has subdermal tissue 130 integrated into and around it from the donor site. In this embodiment, skin grafting may occur between the deep dermal portion of the skin at the implantation site and the fully integrated dermal/subdermal tissue in the porous ingrowth collar 98.

The foregoing discussion discloses and describes merely exemplary arrangements of the present teachings. The embodiments described herein are not intended to be limiting in describing the full scope of implant devices and methods of the present technology. Equivalent changes, modifications and variations of embodiments, materials, components, and methods can be made within the scope of the present technology, with substantially similar results. Furthermore, the mixing and matching of features, elements, and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings.

What is claimed is:

1. A transdermal implant assembly for attaching an external prosthesis to a bone of a patient, the transdermal implant assembly comprising:
   a transdermal bone fixator configured for anchoring into a recess of the bone, the transdermal bone fixator including:
      a longitudinally extending shaft configured to be received into the recess of the bone;
      a spindle defining a cavity, the spindle having a proximal end and a distal end, wherein the distal end extends a distance past a dermis layer of the patient and is exposed to an environment external from the patient;
      a compliant biasing member disposed within the cavity; and
      an end cap removably coupled to the spindle and configured to seal the cavity;
   a prosthesis adapter coupled to the spindle and configured for connection to an external prosthetic device that is operable for use with the bone,
   wherein the compliant biasing member is accessible upon removal of the end cap for adjustments from the external environment.

2. The transdermal implant assembly of claim 1, further comprising at least one sensor configured to measure an operational parameter of the transdermal implant.

3. The transdermal implant assembly of claim 2, wherein the at least one sensor comprises a force sensor configured to measure a parameter of the compliant biasing member.

4. The transdermal implant assembly of claim 2, wherein the at least one sensor is responsive to infections in the implant and monitors at least one physiological parameter selected from the group consisting of temperature, pressure, pH, electrical potential, and oxygen saturation.

5. The transdermal implant assembly of claim 2, wherein the at least one sensor is configured to transmit data using wireless communication technology.

6. The transdermal implant assembly of claim 1, further comprising an ingrowth collar disposed between the shaft and the proximal end of the spindle and configured for transcutaneous implantation.

7. The transdermal implant assembly of claim 6, wherein the ingrowth collar comprises porous titanium.

8. The transdermal implant assembly of claim 1, wherein the ingrowth collar comprises a biocompatible coating providing a substantially dome-shaped profile disposed adjacent the dermis layer.

9. The transdermal implant assembly of claim 1, further comprising an anchor fully retained within the recess of the bone and configured to secure the transdermal bone fixator to the bone, the anchor including a stem portion extending through the shaft of the transdermal bone fixator and into the cavity of the spindle.

10. The transdermal implant assembly of claim 9, further comprising an adjustment nut coupled to the stem portion of the anchor and configured to adjust a force exerted by the compliant biasing member.

11. The transdermal implant assembly of claim 10, wherein the end cap is configured to be removed to allow access to the adjustment nut transdermally for adjusting the force after implantation of the transdermal bone fixator.

12. The transdermal implant assembly of claim 1, wherein an exterior of the spindle is tapered and the distal end of the spindle is coupled with a tapered bore defined within the prosthesis adapter.

13. The transdermal implant assembly of claim 1, wherein the shaft, spindle, and ingrowth collar of the transdermal fixator are formed as a monolithic component.

14. The transdermal implant assembly of claim 1, further comprising at least one channel in fluid communication with both the cavity of the spindle and the recess of the bone.

15. The transdermal implant assembly of claim 1, further comprising a centering sleeve having an outer surface configured to engage with the recess in the bone and an inner surface configured to receive the longitudinally extending shaft of the transdermal bone fixator.

16. A transdermal implant assembly for attaching an external prosthesis to a bone of a patient, the transdermal implant assembly comprising:
    an anchor disposed in and secured to a recess formed in the bone, the anchor including a longitudinally extending stem;
    a transdermal bone fixator coupled to the anchor, the transdermal bone fixator including:
        a longitudinally extending shaft configured to be received into the recess formed in the bone;
        a spindle defining a cavity, the spindle having a proximal end and a distal end, wherein the distal end extends a distance past a dermis layer of the patient and is exposed to an environment external from the bone of the patient;
        a compliant biasing member disposed within the cavity, wherein the compliant biasing member is pre-stressed and configured to provide a compressive force to the bone;
        an adjustment member disposed in the cavity and threadably coupled to the longitudinally extending anchor stem, the adjustment member being accessible from the external environment for adjusting the compliant biasing member without removing the spindle;
    a prosthesis adapter coupled to the spindle and configured for connection to an external prosthetic device that is operable for use with the bone.

17. The transdermal implant assembly of claim 16, further comprising an end cap removably coupled to the spindle and configured to seal the cavity.

18. The transdermal implant assembly of claim 16, further comprising an adjustment tool configured to engage the adjustment member after the transdermal bone fixator is implanted.

19. The transdermal implant assembly of claim 16, wherein the adjustment tool is configured to be manipulated external to the transdermal bone fixator and engage and move the adjustment member only by removing one member connected to the transdermal bone fixator.

20. A method of implanting a transdermal implant assembly into a patient, the method comprising: exposing and preparing a bone to receive a transdermal bone fixator; the transdermal bone fixator comprising: a longitudinally extending shaft configured to be received into the bone; and a spindle having a proximal end and a distal end, wherein the distal end is configured to extend a distance past a dermis layer of the patient; a compliant biasing member disposed within an interior of the spindle; implanting the shaft of the transdermal bone fixator into the bone; exposing at least a portion of the spindle to an environment external from the patient; setting the compliant biasing member to exert a first force; monitoring the force of the compliant biasing member; and accessing the interior of the spindle and adjusting the compliant biasing member to exert a second force after the transdermal implant assembly is implanted in the bone of the patient.

21. The method of claim 20, further comprising:
    implanting, below the dermis layer of an implantation site, a porous ingrowth member and closing the implantation site, allowing the dermis layer to integrate with the porous ingrowth member prior to exposing and preparing the bone;
    resecting an area of the dermis layer adjacent to and including the porous ingrowth member; and
    implanting the transdermal bone fixator, wherein at least a portion of the spindle is configured to pass through a bore defined in the porous ingrowth member.

22. The method of claim 21, wherein the bore of the porous ingrowth member and an exterior of the spindle define mating tapered surfaces operable to provide a tapered junction between the bore and spindle, and the method further comprises providing at least one elastomeric sealing member at the tapered junction.

23. The method of claim 20, wherein accessing the interior of the spindle comprises removing an end cap of the transdermal implant assembly.

* * * * *